(12) United States Patent
Soltanpour et al.

(10) Patent No.: US 6,589,198 B1
(45) Date of Patent: Jul. 8, 2003

(54) IMPLANTABLE MICRO-PUMP ASSEMBLY

(76) Inventors: David Soltanpour, 5 Lindsley Dr., Larchmont, NY (US) 10538; Mohsen Shahinpoor, 9910 Tanoan Dr. NE., Albuquerque, NM (US) 87111

( * ) Notice: Subject to any disclaimer, the term of this patent is extended or adjusted under 35 U.S.C. 154(b) by 0 days.

(21) Appl. No.: 09/586,962

(22) Filed: Jun. 5, 2000

Related U.S. Application Data

(63) Continuation-in-part of application No. 09/015,759, filed on Jan. 29, 1998, now Pat. No. 6,168,575.

(51) Int. Cl.⁷ .................................................. A61M 5/00
(52) U.S. Cl. ................... 604/9; 604/8; 604/151
(58) Field of Search .......................... 604/8, 9, 10, 119, 604/151, 123, 131, 149; 623/14.13, 3.12, 6.14, 23.68

(56) References Cited

U.S. PATENT DOCUMENTS

| | | | | |
|---|---|---|---|---|
| 4,652,265 A | * | 3/1987 | McDougall | 623/24 |
| 5,073,094 A | * | 12/1991 | Dorman et al. | 417/412 |
| 6,203,291 B1 | * | 3/2001 | Stemme et al. | 137/833 |

* cited by examiner

*Primary Examiner*—Angela D. Sykes
*Assistant Examiner*—Leslie R. Deak
(74) *Attorney, Agent, or Firm*—Alfred F. Hoyte, Jr.

(57) ABSTRACT

Self-powered, bio- implantable, pressure adjustable mini-pump systems for medical applications including body fluid pressure control, drainage control, and drug delivery systems. The mini-pump systems include a primary mini-pump chamber having an anterior end attached to an implantable intake conduit. The device of the invention is further equipped with an adjustable variable flow valve or shunt in the form of a first cantilever slab, in combination with an anterior end one-way valve in the form of another cantilever slab. The posterior end of the mini-pump chamber is connected to a drainage conduit, via another one-way valve. Opposing diaphragm elements in the form of a pair of oscillatory flexing miniature ionic polymer metal composite IPPC artificial muscles, is used to vary the volume of the primary mini-pump chamber and thereby effect pumping action. A key feature of the invention is a secondary power generation system, which, in one embodiment of the invention comprises a relatively large piece of IPPC artificial muscle which, for certain types of implants, may be attached to local muscle tissue. Contraction and expansion of the local muscle tissue causes flexure of the IPPC artificial muscle, thereby generating a voltage for driving the diaphragm elements.

26 Claims, 3 Drawing Sheets

IMPLANTABLE MICRO-PUMP ASSEMBLY

CROSS REFERENCE TO RELATED APPLICATIONS

This application is a continuation in part of application Ser. No. 09/015,759, filed on Jan. 29, 1998. Now 6,168,575.

BACKGROUND OF THE INVENTION

1. Field of the Invention

The present invention relates to miniature implantable pumps. More specifically, it relates to improved miniature implantable pumps which may be used as bio-compatible medical implants for controlling diseases such as glaucoma and for controlled delivery of drugs.

2. Description of the Prior Art

Mechanical and electro-mechanical medical implants are well known and, depending upon the type, have met with varying success rates. One problem with these devices is the lack of a reliable, long term power source. Ideally, the power source should last for the life of the implant, as many of these implants require invasive procedures both to install and maintain. Indeed, an external power source is virtually impossible in many situations.

One use for mechanical implants is the treatment of glaucoma. Glaucoma is a common eye disease which is caused by excessive ocular pressure in the anterior chamber of the eyeball. Many devices and techniques have been devised in order to control this pressure. The devices fall generally into two types; passive devices such as a simple tubular shunts or similar device which drains aqueous humor from the anterior chamber, and active devices which have means for controllably draining ocular pressure, the systems typically using check valves or similar mechanical devices. While these systems are somewhat effective, they all tend to suffer from the drawback in that they are unreliable or require frequent maintenance which always involves a fairly invasive procedure. Failure to properly maintain the devices can result in long term damage to the eye.

Recently, mechanical devices have been used in order to effect controlled delivery of drugs. These devices are almost all passive, with the exception of a few highly experimental devices such as nanobots. Mechanical devices, while possessing many advantages, are rarely used as the reliability of passive devices is already established, albeit with the aforementioned shortcomings.

U.S. Pat. No. 5,370,607 issued to Memmen discloses a glaucoma implant device which has a tubular shunt for draining fluid from the eye. By contrast, the present invention contemplates a controllable, self powered pumping mechanism for draining fluid from the eye to treat glaucoma.

U.S. Pat. No. 4,911,616 issued to Laumann, Jr. discloses a microminiature pump which may be used to administer medications in sensitive locations in the body such as the eye. The pump is programmable, but the patent does not disclose which aspects of the pump operation can be controlled. Also, the pump requires a separate power source. By contrast, the present invention contemplates a miniature pump and conduit assembly which may be used, among other things, to control glaucoma by controllably pumping fluid from the eye in accordance with sensed pressure conditions within the eye.

U.S. Pat. No. 5,062,841 issued to Siegel discloses an insulin pump which can be used to pump insulin directly into the bloodstream in response to blood glucose levels. By contrast, the present invention contemplates a self powered miniature pump which can be implanted into the tissue surrounding the eye and can controllably reduce ocular pressure.

U.S. Pat. No. 5,433,701 issued to Rubinstein discusses an active ocular pressure control device which includes a pump which is selectively operated in response to a control signal from a pressure sensor. However, no details as to the power source or structure of the pump, microprocessor, or pressure sensing means are disclosed.

None of the above inventions and patents, taken either singly or in combination, is seen to describe the instant invention as claimed.

SUMMARY OF THE INVENTION

The present invention concerns self-powered, implantable, pressure adjustable mini-pump systems for intraocular pressure control for glaucoma patients as well as other medical applications requiring body fluid pressure, drainage control and drug delivery systems. These mini-pump systems include a primary mini-pump chamber whose anterior end is attached to an implantable intake conduit. In the case of an ocular pressure control device, the intake conduit is inserted into the anterior chamber of the eye. The device of the invention is further equipped with an adjustable variable flow valve or shunt in the form of a first cantilever slab, in combination with an anterior end one-way valve in the form of another cantilever slab. A mini-pump composed of a pair of oscillatory flexing miniature ionic polymer metal composite IPPC artificial muscle, is used to pump fluid or dispense medications. The posterior end of the mini-pump chamber is connected to a drainage conduit, via yet another one-way valve, to drain local bodily fluids out to a flat fan-shaped distribution plate. A key feature of the invention is a secondary power generation system in the form of either a much larger piece of IPPC artificial muscle which, in the case of glaucoma prevention systems, may be placed on the globe surface (sclera) of the eye and attached to and secured by the extraocular muscles of the eye. An alternative external power system includes a biocompatible induction coil with gold wire armature that can be transcutanously activated, adjusted, and computer-interrogated and controlled by a surgeon. The power generated in the larger IPPC artificial muscle by random eye muscle motion maybe used to power the mini-pump to automatically drain excess aqueous humor from the anterior chamber through the mini-pump chamber. Alternatively, the power generating artificial muscle is replaced by a power generation induction coil made with gold wires. The power generated by the induction coil transcutanously from outside of the eye by a microprocessor and computer-controlled power induction system can be used by both the patient and or the opthamologist/surgeon to continuously interrogate and monitor the intraocular pressure in the anterior chamber and to enable the mini-pump, to pump out excess aqueous humor from the pressurized anterior chamber of a glaucoma patient. If the pump is used to administer drugs, the artificial muscle may be used to derive power from local musculature, and information concerning the amount and time of dispensing, among other things, may be obtained. A pressure regulating system including a pressure sensor and pump controlling microprocessor may also be used with the inventive system.

A new class of ionic polymer metal composite (IPMC) artificial muscles has been developed at the University of New Mexico Artificial Muscles Research Institute (AMRI). IPMC micro-actuators and sensors have been designed, fabricated and successfully tested. These artificial muscles are made from ionic polymeric (polyelectrolyte) gels chemically treated with platinum (IPPC). They exhibit large motion sensing and actuation capabilities in a distributed manner. IPMCs are three-dimensional networks of cross-linked macromolecular polyelectrolytes with internal electrodes that swell, shrink, bend or generally deform in an electric field. Conversely, IPMCs are capable of generating an electric field or voltage as a result of being manipulated. Thus, direct computer control and monitoring of large expansions and contractions of ionic polymeric gel-noble metal composite muscles by means of voltage controller has been achieved. In fact, they require only a few volts for actuation. These muscles can be cut as small as needed and still preserve their functional properties. Accordingly, this technology is incorporated into the present invention as will be explained in more detail later.

Accordingly, it is a principal object of the invention to provide an implantable, self powered, miniature pump.

It is a major object of this invention to provide an implantable pump assembly and associated method for controlling intraocular pressure.

It is another object of the invention to provide such a pump assembly having an automatically controlled pumping rate.

It is still another object of the invention to provide an improved, biologically implantable pump assembly having a pumping rate which is controllable in response to sensed local pressure conditions.

It is another object of the invention to provide an implantable pump assembly which can derive electrical power from muscle movement.

It is another object of the invention to provide an implantable pump assembly which can administer drugs.

It is another object of the invention to provide a miniature pumping system for controlling ocular pressure having means to generate power from the movement of the ocular muscle.

It is another object of the invention to provide a miniature pumping system which can be interrogated electronically while remaining implanted in the body.

It is another object of the invention to provide an improved method and apparatus for controlling glaucoma including a micropump which is implanted into the anterior chamber of the eye.

It is another object of the invention to provide an improved method and apparatus for controlling glaucoma including a micropump where pump operation is controlled in accordance with the disease state of the optic nerve and the sensed ocular pressure.

It is yet another object of the invention to provide an improved, biologically implantable pump assembly having a draining tube with a relatively wide outlet end to disperse the outflow of fluid.

It is yet another object of the invention to provide an improved, biologically implantable pump assembly having constant flow therethrough to prevent occlusion of the drainage tube.

Finally, it is a general object of the invention to provide improved elements and arrangements thereof in an apparatus for the purposes described which is dependable and fully effective in accomplishing its intended purposes.

These and other objects of the present invention will become readily apparent upon further review of the following specification and drawings.

BRIEF DESCRIPTION OF THE DRAWINGS

Various other objects, features, and attendant advantages of the present invention will become more fully appreciated as the same becomes better understood when considered in conjunction with the accompanying drawings, in which like reference characters designate the same or similar parts throughout the several views, and wherein.

DETAILED DESCRIPTION OF THE PREFERRED EMBODIMENTS

Figure 1:
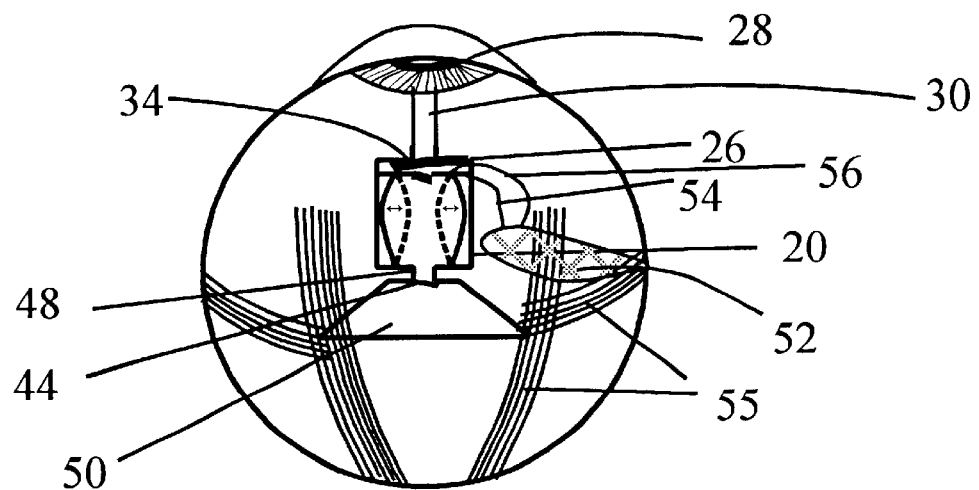
FIG. 1 is a side elevational view of a human eye upon which the device of the present invention has been implanted.

Referring now to FIGS. 1–4, a pump assembly, generally indicated by the numeral 10, is shown implanted in accordance with the method of the present invention. The assembly 10 must be sufficiently small to be implanted in the body without causing undue discomfort to the patient, and yet be able to generate or store enough energy to pump fluid for a relatively long time. The size of the assembly should be on the order of 10 cubic mm in volume.

The assembly 10, has a pump 12 with a housing 20, which is made from biocompatible titanium or other biocompatible, corrosion resistant metal. Of course, all of the electronics must be contained within a hermetically sealed housing as will be explained in more detail later. Fluid displacement through the pump 12 is effected by a pair of cooperating IPPC artificial muscles 22, 24. The anterior end 26 of the pump housing 20 is fluidly coupled to an intake conduit 30 which is inserted into the anterior chamber of the eye 28.

A series of cantilever slabs functioning as check valves operate to control fluid flow through the pump 12. A first cantilever slab or valve 34 is placed at the anterior end 26 of the pump. A second cantilever valve 36 is placed across an opening 38 formed in a fluid barrier 40 which serves to separate the anterior end 26 of the pump 12 from the interior chamber 42 of the pump 12. A third cantilever valve 44 is placed at the outlet of a discharge conduit 48 which is positioned at the posterior end 47 of the housing 20 the discharge conduit 48 fluidly coupled to the interior chamber 42. The discharge conduit 48 is fluidly coupled to a fan shaped discharge end 50 to disperse the effluent fluid. The fan shaped end 50 helps to reduce the possibility of fibrosis. Accordingly, the possibility of occlusion of the drainage conduit 48 is reduced. Additionally, antifibroblastic agents may be applied after surgery to prevent fibrosis. It should be noted that the intake and drainage conduits 30, 48 must be of sufficient diameter to accommodate the required fluid flow. It can be readily appreciated that the constant fluid flow associated with the inventive method will help to keep the conduits free of blockage.

The first cantilever slab 34 operates to regulate fluid flow through the pump 10 by setting a minimum IOP for pump operation. The minimum IOP (intra-ocular pressure) is preferably around 10 mm Hg. It should be noted that this passive pressure regulating system may be used as a supplement or backup system for an electronic pressure regulating system as will be explained in more detail later. Threshold adjusting pins 49 are used to secure cantilever slab 34 to an interior surface 31 of housing 20. Threshold adjusting means such as pins 49 may be employed to allow for adjustable setting of the minimum IOP. When the IOP is below the preset threshold, the valve 34 will be in the shutoff position and no fluid flow through the pump can occur. It can be readily appreciated that an electronic sensing means may be employed to sense the IOP, with the artificial muscles 22, 24 being operated only in response to a signal from a microprocessor while the sensed IOP remains above a predetermined threshold. Such a control system is disclosed in application Ser. No. 09/015,759, which is hereby incorporated by reference.

Power to operate the pump 10 may be derived from a surgically implanted artificial muscle 52. Preferably, the artificial muscle 52 is of the IPPC type, as are muscles 22 and 24.

The muscle 52 is surgically attached to at least one of the ocular muscles 53 using standard surgical techniques. As has been previously explained, IPPC artificial muscles can generate a small voltage, on opposite sides, when being bent or otherwise manipulated. This small voltage can be extracted from the IPPC muscle by lead wires attached to opposite sides (surfaces, not edges) of the muscles. The present invention utilizes lead wires 54, 56, to transfer voltage generated by artificial muscle 52 to artificial muscles 22, 24. It can be readily appreciated that, as the voltage generated by artificial muscle 52 will be as random as the movement of the muscles to which it is attached, the voltage generated thereby will be random. Thus, the artificial muscles 22, 24 will be randomly, but constantly, in motion. This random motion will cause constant fluid displacement within the interior chamber 42 of the pump 12. Of course, there will be no actual fluid flow through the interior pump chamber 42 when the IOP is below the predetermined threshold pressure as the cantilever valve 34 will be in the shutoff position. The rate of fluid flow is variable from 0 to about 10 $\mu l$ per minute.

Figure 3B:
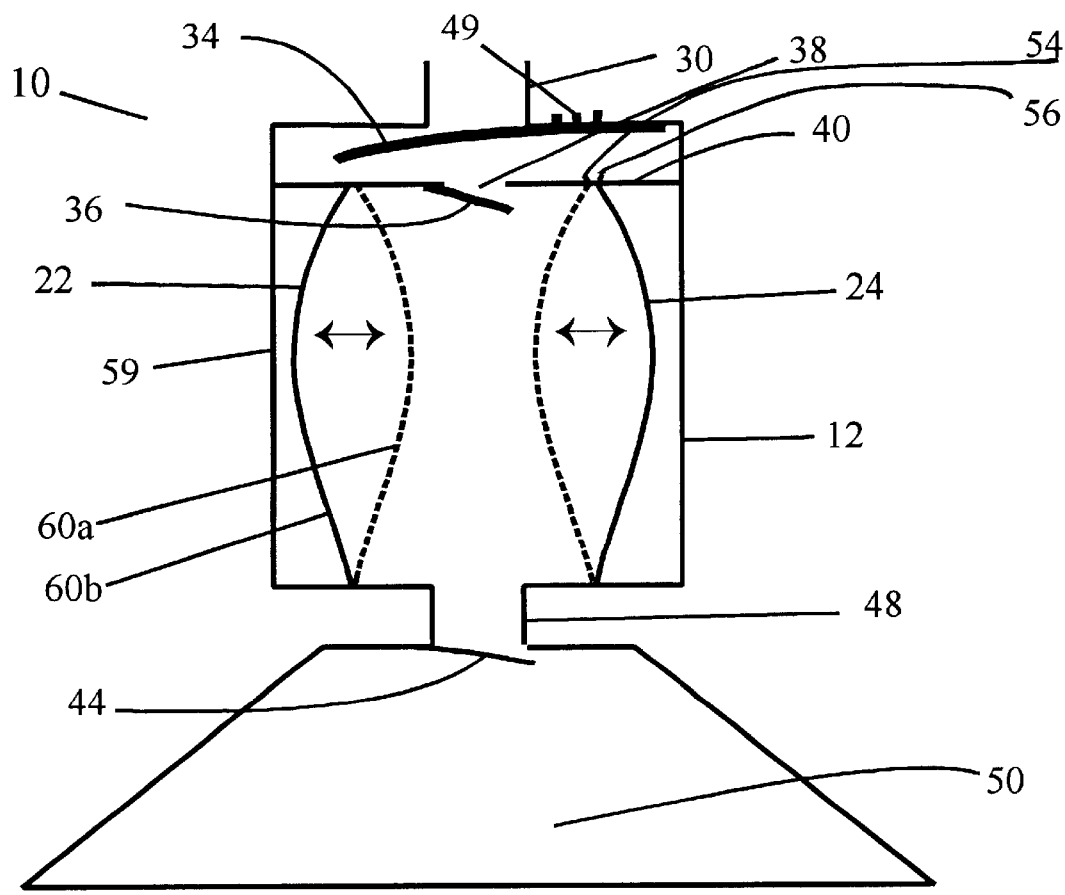
FIGS. 3a and b depict a side view and a detailed sectional view of the pump chamber of the device showing the three cantilever slab type one way valves as well as the active pumping muscles.
Figure 3A:
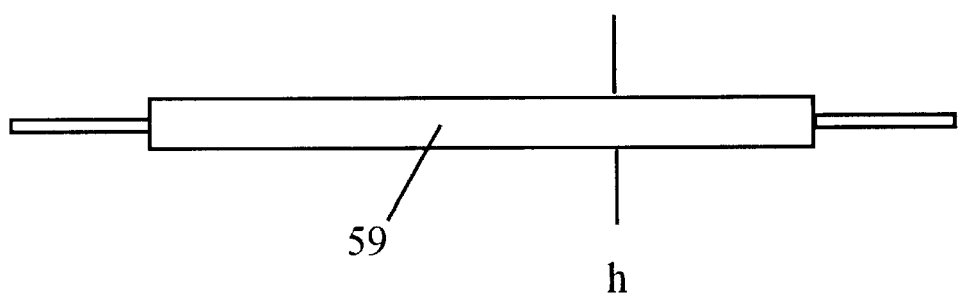

FIGS. 3a and 3b show the pump chamber 42 in greater detail. The pump chamber 42 has a substantially rectangular cross section, with a relatively thin profile having sidewalls 59 of height h as can be seen in FIG. 3a. The width of the artificial muscles 22, 24 is approximately equal to h, so that the movement of the artificial muscles 22, 24, which are in the form of strips having a rectangular shape, is restricted to the transverse flexing as indicated by arrows 60a and b. It should be noted that, in accordance with a key aspect of the invention, fluid flow through the device 10 is fairly constant, thereby preventing the occlusion of both the drainage conduit 48 and the intake conduit 30.

Figure 2:
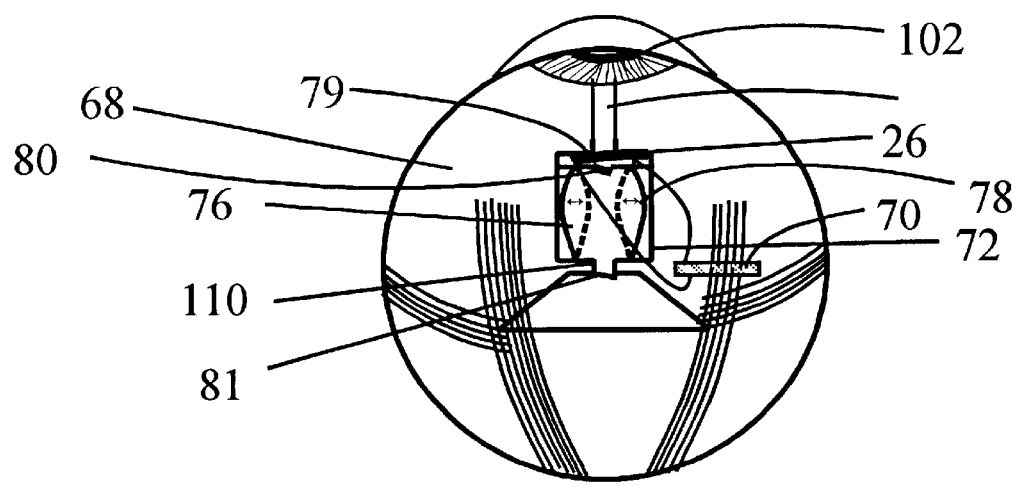
FIG. 2 is another side elevational view of a human eye upon which an alternative embodiment of the device of the present invention has been implanted.
Figure 4:
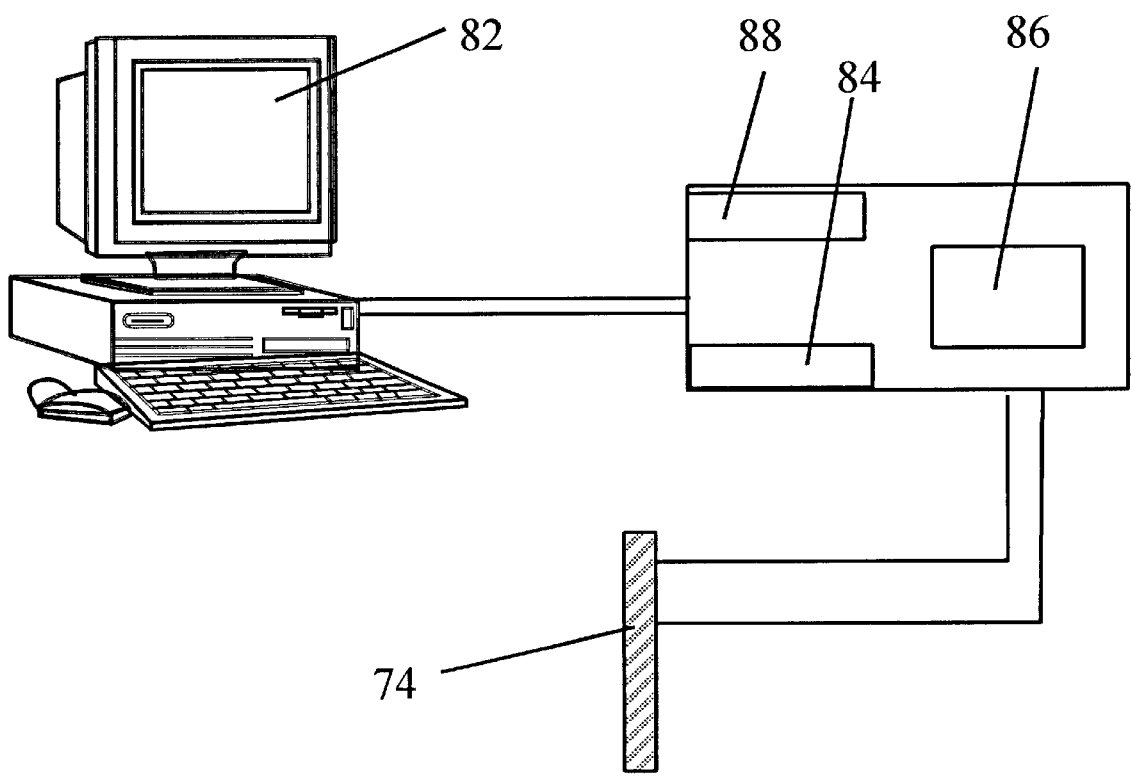
FIG. 4 is a block diagram of components external to the device depicting the interrelationship of the various components.

An alternative embodiment having an external power supply is shown in FIG. 2. The device 68, differs from the first embodiment 10 in that in lieu of power generation muscle 52, an induction coil 70 is implanted in the eye or other region of interest. Power may then be transferred to the pump 72 by applying power to the coil 70 via an external coil 74 as shown in FIG. 4. This arrangement also allows for regulating the motion of the artificial muscles 76, 78, which function in exactly the same manner as muscles 22, 24. Valves 79, 80, and 81 also function in the same manner as valves 36, 34, and 44. A computer or dedicated microprocessor device 82, having a power supply 84, a voltage regulator 86, and a signal generating and processing means 88 all operably connected thereto, can receive signals from as well as send signals to the pump 72. Thus the pump 72 may be interrogated and its pumping action controlled in response to sensed conditions as will be explained in more detail later.

In operation, after the surgeon has implanted the device 10, the excess pressure in the anterior chamber 100, causes the aqueous humor to flow inwardly through the conduit 30, into the mini-pump chamber 42. One-way adjustable cantilever valve 34 is set, using, e.g. pins 49 such that the flow out of the intake pipe 30 into the chamber 42 is almost a linear function of the anterior chamber pressure (IOP). Furthermore, the one-way valve 34 is adjustable so that below, say, 10 mm Hg of pressure the drainage flow rate is zero. Note that the aqueous humor in the pump chamber 42 is pumped out by the random flapping of the mini-pump muscles 22, 24 created by the random motion of the larger power generation muscle 52, which is secured under the extraocular muscles of the eye 53, as well as the cooperative actions of the one-way valves 36 and 44. The excess fluid is then pumped out through the out conduit 48 in to the distribution plate 50. In this configuration the device 10 is only actively pumping if there is any fluid in the chamber 42, and there is always fluid in the chamber if the IOP rises above the predetermined threshold pressure of say 10 mm Hg.

Referring now to FIG. 2, in this embodiment the operation of the invention proceeds as follows. After the surgeon has implanted the device 10 the excess pressure in the anterior chamber 102, causes the aqueous humor to flow into and through the intake conduit 104 into the pump chamber 106. As in the previous embodiment, one-way adjustable cantilever valve 79 is set such that the flow out of the intake pipe 104 into the chamber 106 is almost a linear function of the anterior chamber pressure (IOP). Furthermore, the one-way valve 79 is adjustable so that below, say, 10 mm Hg of pressure the drainage flow rate is zero. Note that the aqueous humor in the pump chamber 106 is pumped out by the flapping of the mini-pump muscles 76,78 created by the transcutanously inducted power to gold coil 70, which is secured under the extraocular muscles of the eye as well as the cooperative actions of the one-way valves 80 and 81. The excess fluid is then pumped out through the out tube 110 to the distribution plate 112. In this manner the device is only actively pumping if there is any fluid in the chamber 106 and there is liquid in the chamber if the IOP rises above a certain threshold pressure of 10 mm Hg. Here any pressure in the chamber 106 causes the muscles 76, .78 to send a sensing signal out, through the induction coil 70 to the outside coil 74 (shown in FIG. 4) and picked up by the microprocessor-controlled voltage regulator (shown in FIG. 4) to enable the patient or the doctor to monitor and possibly activate the pump 68 to pump the excess liquid from the chamber 106. It should be noted that the sensing signal is a result of the flexing of the muscles as has been previously discussed.

In accordance with a third embodiment of the invention, a pressure sensing device and associated microprocessor (not shown) may be employed to sense the ocular pressure and to drive the assembly 10, 68 in accordance with the sensed pressure. Such a pressure sensor would have to be sensitive enough to detect changes on the order of 1 mm Hg. Preferably, the pressure sensor and microprocessor would be operated from the same power source as the pump assembly 10, 68.

It is to be understood that the provided illustrative examples are by no means exhaustive of the many possible uses for my invention. For example, power generated by the artificial muscle 52 may be used to provide power for an artificial retina or other electronic ocular implant.

From the foregoing description, one skilled in the art can easily ascertain the essential characteristics of this invention and, without departing from the spirit and scope thereof, can make various changes and modifications of the invention to adapt it to various usages and conditions.

It is to be understood that the present invention is not limited to the sole embodiment described above, but encompasses any and all embodiments within the scope of the following claims.

We claim:

1. A bio- implantable pump assembly for ocular implantation to selectively reduce ocular pressure comprising:
   a main body having an interior chamber with an intake conduit and a discharge conduit coupled thereto to allow for fluid flow into and through said interior chamber;
   a first valve means for selectively allowing a fluid to flow into said interior chamber from said intake conduit, and a second valve means for selectively allowing said fluid to discharge from said interior chamber through said discharge conduit; and, fluid displacement means comprised of artificial muscle disposed within said main body for generating pressure to pump said fluid.

2. The assembly of claim 1 wherein said displacement means is electrically connected to a source of electrical power.

3. The assembly of claim 1 wherein said first valve is a flow regulator.

4. The assembly of claim 3 wherein said flow regulator is an adjustable check valve.

5. The assembly of claim 2 wherein said source of electrical power is a second artificial muscle disposed exteriorly of said main body.

6. The assembly of claim 5 wherein said second artificial muscle generates a voltage in response to bending and twisting forces.

7. The assembly of claim 6 wherein said assembly is positioned in an implant area, and said second artificial muscle is adapted for attachment to muscle or tissue proximate the implant area, whereby movement of said muscle or tissue causes said bending and twisting forces to be applied to said second artificial muscle.

8. The assembly of claim 1 wherein said displacement means is formed from a pair of mutually opposed strips of ionic polymer metal composite IPPC material.

9. The assembly of claim 1 wherein said displacement means is formed from a pair of mutually opposed strips of artificial muscle material.

10. A bio- implantable pump assembly comprising:
    a main body having an interior chamber with an intake conduit and a discharge conduit fluidly coupled thereto to allow for fluid flow into and through said interior chamber;
    a first valve means for selectively allowing a fluid to flow into said interior chamber from said intake conduit, and a second valve means for selectively allowing said fluid to discharge from said interior chamber through said outlet; and,
    a fluid displacement means connected to a source of power for generating pressure to pump said fluid;
    wherein said source of power for said fluid displacement means is an artificial muscle.

11. The assembly of claim 10 wherein said artificial muscle is a strip of ionic polymer metal composite IPPC material.

12. The assembly of claim 10 wherein said artificial muscle generates electrical power in response to bending and twisting forces.

13. The assembly of claim 12 wherein said assembly is positioned in an implant area, and a secondary artificial muscle is adapted to be attached to muscle or tissue proximate the implant area, whereby movement of said muscle or tissue causes said bending and twisting forces to be applied to said secondary artificial muscle.

14. The assembly of claim 10 wherein said fluid displacement means is formed from a pair of mutually opposed strips of ionic polymer metal composite IPPC material.

15. The assembly of claim 10 wherein said fluid displacement means is formed from a pair of mutually opposed strips of artificial muscle material.

16. The assembly of claim 10 wherein said first valve means is an adjustable check valve.

17. A bio- implantable pump assembly comprising:
    a main body having an interior chamber;
    an intake conduit and a discharge conduit extending from said main body and fluidly coupled to said interior chamber to allow for fluid flow into and through said interior chamber;
    a first valve means for selectively allowing a fluid to flow into said interior chamber through said intake conduit, and a second valve means for selectively allowing said fluid to discharge from said interior chamber through said discharge conduit; and,
    a fluid displacement means disposed within said interior chamber for generating pressure to pump said fluid; and,
    an artificial muscle means electrically connected to said fluid displacement means for supplying electrical power thereto.

18. A bio- implantable pump assembly for implantation into an anterior chamber of an eye for controlling ocular pressure comprising:
    a main body having an interior chamber with an intake conduit and a discharge conduit to allow for fluid flow into and through said interior chamber; and,
    an fluid displacement means comprised of artificial muscle disposed within said main body for generating pressure to pump said fluid.

19. The assembly of claim 18 including a first valve means for selectively allowing a fluid to flow into said interior chamber from said intake conduit, and a second valve means for selectively allowing said fluid to discharge from said interior chamber through said discharge conduit.

20. The assembly of claim 18 wherein said displacement means is electrically connected to a source of electrical power.

21. The assembly of claim 20 wherein said source of electrical power is a second artificial muscle.

22. The assembly of claim 21 wherein said second artificial muscle generates a voltage in response to bending and twisting forces.

23. The assembly of claim 22 wherein said assembly is positioned in an implant area, and said second artificial muscle is adapted for attachment to muscle or tissue proximate the implant area, whereby movement of said muscle or tissue causes said bending and twisting forces to be, applied to said second artificial muscle.

24. The assembly of claim 18 wherein said first valve means is a flow regulator.

25. The assembly of claim 24 wherein said flow regulator is an adjustable check valve.

26. The assembly of claim 18 wherein said artificial muscle fluid displacement means is formed from a pair of mutually opposed strips of ionic polymer metal composite IPPC material.

* * * * *